United States Patent [19]

Versic

[11] Patent Number: 5,393,533
[45] Date of Patent: Feb. 28, 1995

[54] PHARMACEUTICALS MICROENCAPSULATED BY VAPOR DEPOSITED POLYMERS AND METHOD

[75] Inventor: Ronald J. Versic, Dayton, Ohio

[73] Assignee: The Ronald T. Dodge Company, Dayton, Ohio

[21] Appl. No.: 124,782

[22] Filed: Sep. 21, 1993

Related U.S. Application Data

[63] Continuation of Ser. No. 753,002, Aug. 23, 1991, Pat. No. 5,288,504, which is a continuation of Ser. No. 243,064, Sep. 9, 1988, abandoned.

[51] Int. Cl.$^6$ ................................................ A61K 9/16
[52] U.S. Cl. ........................... 427/2.19; 424/458; 424/469; 424/449; 424/451; 424/497; 427/213
[58] Field of Search ............... 424/497, 458; 427/469, 427/2, 3, 213

[56] References Cited

U.S. PATENT DOCUMENTS

| | | | |
|---|---|---|---|
| 3,117,168 | 1/1964 | Gorham | 260/668 |
| 3,149,175 | 9/1964 | Pollart | 260/670 |
| 3,153,103 | 10/1964 | Yeh | 260/671 |
| 3,155,712 | 11/1964 | Yeh | 260/465 |
| 3,164,625 | 1/1965 | Pollart | 260/465 |
| 3,221,068 | 11/1965 | Gorham | 260/649 |
| 3,235,516 | 2/1966 | Leonard, Jr. | 260/2 |
| 3,240,722 | 3/1966 | Orttung, Jr. et al. | 260/2 |
| 3,246,627 | 4/1966 | Loeb et al. | 118/49 |
| 3,247,274 | 4/1966 | Pollart | 260/670 |
| 3,258,504 | 6/1966 | Lenaers et al. | 260/668 |
| 3,268,599 | 8/1966 | Chow | 260/649 |
| 3,271,470 | 9/1966 | Spence et al. | 260/670 |
| 3,271,471 | 9/1966 | Baker et al. | 260/670 |
| 3,274,267 | 9/1966 | Chow | 260/649 |
| 3,280,202 | 10/1966 | Gilch | 260/648 |
| 3,288,728 | 11/1966 | Gorham | 260/2 |
| 3,297,591 | 1/1967 | Chow | 260/2 |
| 3,300,332 | 1/1967 | Gorham et al. | 117/100 |
| 3,301,707 | 1/1967 | Loeb et al. | 117/227 |
| 3,311,668 | 3/1967 | Spence et al. | 260/668 |
| 3,319,141 | 5/1967 | Cariou et al. | 317/258 |
| 3,332,891 | 7/1967 | Chow et al. | 260/2 |
| 3,342,754 | 9/1967 | Gorham | 260/2 |
| 3,349,045 | 10/1967 | Gilch | 260/2 |
| 3,349,147 | 10/1967 | Clay et al. | 260/680 |
| 3,375,110 | 3/1968 | Loeb | 96/36 |
| 3,379,803 | 4/1968 | Tittmann et al. | 264/81 |
| 3,395,016 | 7/1968 | Loeb | 96/36 |
| 3,397,085 | 8/1968 | Cariou et al. | 117/217 |
| 3,399,124 | 8/1968 | Gilch | 204/72 |
| 3,405,117 | 10/1968 | Yeh | 260/649 |

(List continued on next page.)

FOREIGN PATENT DOCUMENTS 9002655  3/1990  WIPO ................... B32B 25/00

OTHER PUBLICATIONS

Schmidt, E. M.: *J. Electrophysiol. Tech.*, 10:19-29 (1983)–"Parylene as an Electrode Insulator: A Review".

Loeb, G. E. et al., *IEEE Trans. on Biomedical Eng.*, BME-24(2):121-128 (Mar., 1977)–"Parylene as a Cronically Stable, Reproducible Microelectrode Insulator".

Gorham, W. F. et al.: *Encyl. Polymer Science*, 15:98-124 (1971).

149th ACS National Meeting, Polymer Chemistry: *C & EN*, 51-52 (Apr. 12, 1965).

*Electronics Letters*, 17(16):81080558 (Jun. 2, 1981).

Kaizer Chemicals, Brochure IC-122.

(List continued on next page.)

*Primary Examiner*—D. Gabrielle Phelan
*Attorney, Agent, or Firm*—Holland & Knight

[57] ABSTRACT

A microencapsulated pharmaceutical is formed by vapor depositing a polymeric film about an active pharmaceutical agent. The film thickness of the vapor deposited film is controlled to provide effective controlled release of said pharmaceutical agent subsequent to application. In a preferred embodiment the pharmaceutical is an orally ingestible pharmaceutical formed by vapor deposition of a poly-p-xylylene polymer about a core comprising an active pharmaceutical agent. The pharmaceutical agent exhibits surprising controlled release activity inspite of the extreme inertness of vapor deposited films such as Parylene films.

2 Claims, 1 Drawing Sheet

U.S. PATENT DOCUMENTS

| | | | |
|---|---|---|---|
| 3,409,410 | 11/1968 | Spence et al. | 23/284 |
| 3,412,167 | 11/1968 | Lewis | 260/668 |
| 3,429,739 | 2/1969 | Tittmann et al. | 117/106 |
| 3,440,295 | 4/1969 | Capitano et al. | 260/668 |
| 3,472,795 | 10/1969 | Tittmann et al. | 260/2 |
| 3,491,142 | 1/1970 | Yeh et al. | 260/469 |
| 3,503,903 | 1/1970 | Shaw et al. | 260/2 |
| 3,509,075 | 4/1970 | Niegisch et al. | 260/2 |
| 3,523,839 | 8/1970 | Shechter et al. | 149/7 |
| 3,556,881 | 1/1971 | Gorham et al. | 149/7 |
| 3,573,968 | 4/1971 | Loeb et al. | 111/106 |
| 3,600,216 | 8/1971 | Stewart | 117/72 |
| 3,754,015 | 8/1973 | Hedaya | 260/456 P |
| 3,764,018 | 10/1973 | Shaw et al. | 210/500 |
| 3,830,733 | 8/1974 | Spivack et al. | 210/22 |
| 3,840,387 | 10/1974 | Hofer | 117/38 |
| 3,864,202 | 2/1975 | Loeb et al. | 161/162 |
| 3,892,892 | 7/1975 | Hofer | 427/272 |
| 3,895,135 | 7/1975 | Hofer | 427/248 |
| 3,936,531 | 2/1976 | Hofer | 427/49 |
| 4,147,562 | 4/1979 | Chiang et al. | 136/213 |
| 4,500,562 | 2/1985 | Jahn et al. | 427/27 |
| 4,508,760 | 4/1985 | Olson et al. | 427/213.34 |
| 4,758,288 | 7/1988 | Versic | 149/6 |

OTHER PUBLICATIONS

Spivack: M. A.: *Corrosion-NACE,* 26(9):371–375 (Sep. 1970)–"Reaction of Parylene C Coated Lithium with Water Vapor".

Hahn, A. W. et al.: *J. Applied Polymer Science, Applied Polymer Symposium,* 38:55–64 (1984) –"Biocompatiblity of Glow–Discharge–Polymerized Films and Vacuum Deposited Parylene" Union Carbide Brochure (©) 1971, 1974, 1976, 1979, 1985.

Tittmann, F. R. et al.: *Synthetic Biomedical Polymers: Concepts and Applications,* Technomic Publishing Co., 117–131 (1980) – "Parylene Coated Polypropylene Microfibers as Cell Seeding . . . ".

Jayne, W. M., Jr.: *Microencapsulation, Processes and Applications,* 103–113 (1973–74) – "Micro-Encapsulation by Vapor Deposition".

NOVA TRAN Abstrasct, p. 107 (Jan. 23, 1980).

Kunz et al, Journal Chem. Soc., Faraday Trans., 68(1): pp. 140–149 (1972).

PHARMACEUTICALS MICROENCAPSULATED BY VAPOR DEPOSITED POLYMERS AND METHOD

This is a continuation of application Ser. No. 07/753,002, filed Aug. 23, 1991, now U.S. Pat. No. 5,288,504, which is a continuation of application Ser. No. 07/243,064, filed on Sep. 9, 1988, now abandoned.

BACKGROUND

Encapsulation of particulate solids and of liquid droplets is commonly done for purposes of controlled release, environmental protection or rendering inert reactive, toxic or hazardous materials. Coating of pharmaceuticals, pesticides, catalysts and discrete electronic elements are some specific examples of applications involving microencapsulation techniques.

There are many different reasons to coat active pharmaceutical agents. First if the active substance is coated it can mask the taste of unpleasant tasting substances. In other cases, the medicament is encapsulated in forms called enteric formulations to prevent the active substance from being exposed to stomach acids. Erythromycin base is readily destroyed in the presence of stomach acid. Attempts to enterically coat erythromycin base is a common subject of the pharmaceutical literature. Enteric formulations are designed to allow the drug to pass through the acidic environment of the stomach without disintegration and yet disintegrate in the duodeneum. Aspirin is often formulated in enteric forms to prevent it from irritating the lining of the stomach. Commonly used coatings for enteric substances are those of the phthalate family especially cellulose acetate phthalate.

Other reasons that drugs are often encapsulated or formulated in delayed release or sustained release form is to prolong the active lifetime of drugs with a short half life. A drug such as nitrofuradantoin is quickly absorbed by the gut and is quickly eliminated by the kidney. However, it is desirable that the nitrofuradantoin be at a high constant plasma level. Microencapsulation can avoid the requirement that a patient take it more times during the day and thus the problems with patient compliance.

In other instances, the drugs are formulated in delayed release form to lessen toxic effects. If it is released all at once in the gut excessively high levels of drugs may be reached. Whereas if the drug is a sustained release form, a therapeutic level but not a toxic level may be achieved. The literature has many examples of formulations of theophylline to allow a therapeutic dose without toxic symptoms.

There are several different types of microencapsulation techniques employed for encapsulation and microencapsulation of pharmaceuticals.

One such method is pan coating. This is an older method developed in the 1880's. This method is used to coat pharmaceutical tablets as well as candies and the like. The disadvantage with this is that it requires rather large particles on the order of several millimeters to several centimeters in size.

Another method is the Wurster coating method. The Wurster coating is an extremely powerful and versatile method for microencapsulation that was developed by Dale Wurster at the University of Wisconsin in the 1960's. It is often called fluid bed coating. The smallest size that the Wurster coater can use is about 100 microns and more realistically about 150 microns. This requires a solid core and utilizes a fluidized bed of air. This means that any material sensitive to oxygen or moisture would be very difficult to process.

A third method of microencapsulation is spray drying. Spray drying is an older method of microencapsulation than the Wurster coating method. Its actual usage is primarily more in the area of foods such as solid drink mixes. Spray drying requires an excessively large amount of capsule wall on the order of 80% on a volume basis. Spray drying is done at elevated temperatures to remove moisture which means that there is a possibility of degrading temperature sensitive pharmaceuticals.

In employing any of these methods coating uniformity is a constant concern. In the case of the pan coating and Wurster coating the capsule walls are applied as droplets on the order of 40 microns in size and above. The droplet size is more likely to be 100-200 microns. The uniformity of the coating then relies upon the uniformity of depositing these relatively large droplets of wall material. This causes some non-uniformity in the coating when these droplets are large compared to the core material. In the case of spray drying the wall is actually a matrix and the small droplets of core material are embedded in it much as a peanut cluster. Some droplets are close to the surface of the particle and some are very deep within. Further, a wall applied as a liquid must flow on wet. This presents problems around sharp surfaces of the core material. Thus in all of these processes coating uniformity varies substantially.

One form of microencapsulation which has not been utilized for pharmaceuticals is vapor deposition of polymeric films. This technology relates both to the vacuum vapor deposition of polymers such as poly-p-xylylene (Parylene) and also to glow discharge polymerized films such as polyolefins including ethylene and methylene, styrene, chlorotrifluoroethylene, tetrafluoroethylene, tetramethyldisuloxane and the like. These methods are generally disclosed in the "Biocompatability of Glow Discharge Polymerized Films and Vacuum Deposited Parylene" in the *Journal of Applied Polymer Science*: Applied Polymer Symposium 38, 55–64 (1984).

Vapor deposited Parylene is used to coat many different substrates including particulate substrates. The method of coating particulate material with Parylene is disclosed for example in Gorham et al U.S. Pat. No. 3,300,332. Primarily the Parylene is used in applications where absolute protection of the coated substrate is required. Examples of these would be coating of reactive metals such as lithium and sodium, coating of catalysts to prevent reaction and coating of electronic components to prevent environmental degradation of the component. In biological applications the Parylene coatings are used to protect implanted materials and prevent rejection of the materials by the body's defenses. Exemplary applications are disclosed for example in *Synthetic Biomedical Polymers Concepts and Applications* Copyright 1980 Technomic Publishing Co. pp 117-131. Coating of integrated circuits to be implanted in the body is disclosed in *Blood Compatability of Components and Materials in Silicone Integrated Circuits*, Electronic Letters Aug. 6, 1981, 17 (16). The use of Parylene generally in orthopedic uses is also discussed in *Parylene Biomedical Data* a 1975 publication of the Union Carbide Co. Parylene because of its strength, biological compatability and general inertness in physiological environments has made it generally suitable as an orthopedic coating for implant devices and the like. This same durability would suggest that it is unsuitable for pharmaceutical application.

SUMMARY OF THE INVENTION

The present invention is premised on the realization that active pharmaceutical agents can be microencapsulated by vapor deposition of polymeric compositions about the pharmaceutical agent. Even though inert polymeric compositions such as poly-p-xylylenes are deposited on pharmaceutical agents the film thickness can be controlled to provide effective controlled release of the pharmaceutical in a variety of circumstances.

In a preferred embodiment, the present invention encompasses a poly-p-xylylene coated pharmaceutical agent which is orally ingestible. The film thickness is controlled to provide effective time release of the active pharmaceutical, inspite of the extreme inertness of the poly-p-xylylene. Other objects and advantages of the present invention will be further appreciated in light of the following detailed description and drawings wherein:

DETAILED DESCRIPTION OF THE INVENTION

Figure 1:
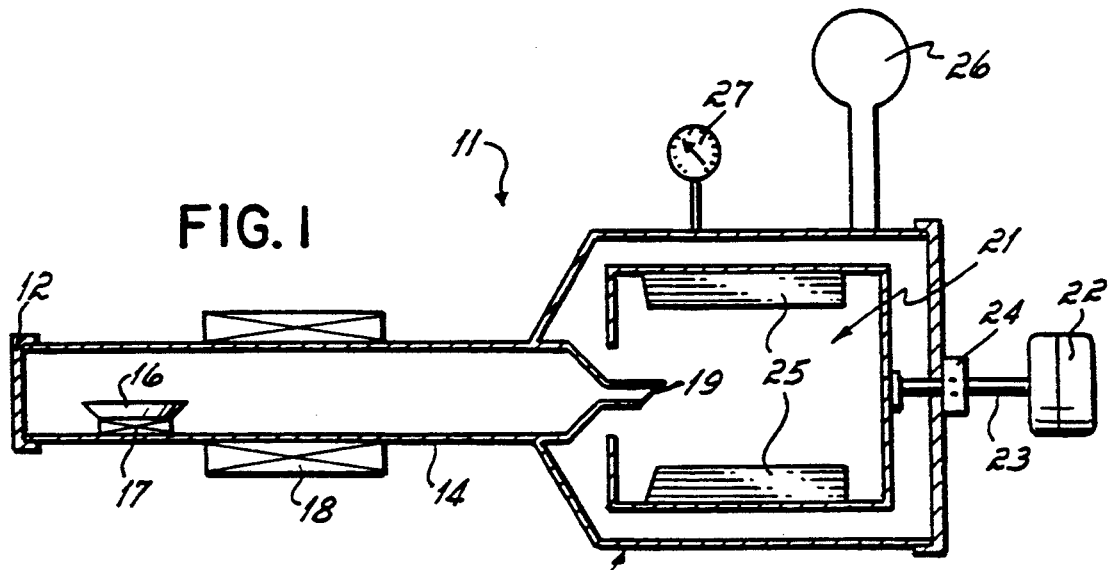
FIG. 1 is a cross-section diagrammatic representation of the apparatus used in the present invention.

The present invention includes a reactive pharmaceutical agent coated with a vapor deposited polymeric film produced by chemical vapor deposition. Chemical vapor deposition in accordance with this invention is used in a broad sense and includes vacuum deposited polymeric films, plasma polymerization deposited polymeric films, glow discharge deposited polymeric films and ultraviolet surface-polymerization deposited polymeric films. Glow discharge films would in turn include both films generated from plasma maintained by radio frequency as well as audio frequency. These polymeric films can include polyethylene, polymethylene, polymethylmethacrylate, silicones such as polydimethylsiloxane, polyfluorinated hydrocarbons such as chlorotrifluoroethylene, tetrafluoroethylene, and also polymers formed from unsaturated monomers such as styrene. The films generated from the method referred to as ultraviolet surface-polymerization are derived from, for instance, hexachlorobutadiene, such as described in Kunz et al: *J. Chem. Soc., Faraday Trans.* 68(1):140–149, (1972), which is incorporated herein by reference in its entirety.

In a preferred embodiment the vapor deposited film is a vacuum deposited polymeric film and more particularly a poly-p-xylylene. A poly-p-xylylene has the following repeating units:

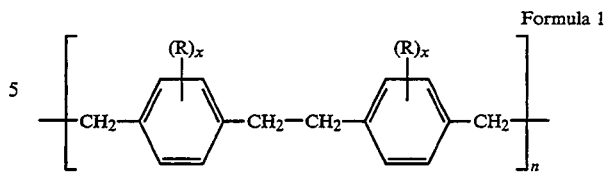

Formula 1 wherein N is 10–10,000 and X is a number from 0 to 3 inclusive and R would represent an aromatic nuclear substituent. Each substituent group R can be the same or different and can be any inert organic or inorganic group which can normally be substituted on aromatic nuclei. Illustrations of such substituent groups are alkyl, aryl, alkenyl, amino, cyano, carboxyl, alkoxy, hydroxylalkyl, carbalkoxy and like radicals as well as inorganic radicals such as hydroxyl, nitro, halogen and other similar groups which are normally substitutable on aromatic nuclei.

Particularly preferred of the substituted groups are those simple hydrocarbon groups such as the lower alkyl such as methyl, ethyl, propyl, butyl, hexyl and halogen groups particularly chlorine, bromine, iodine and fluorine as well as the cyano group and hydrogen, i.e., where X is 0.

These polymers are formed by the pyrolysis and vapor deposition of a di-p-xylylene having the following general formula:

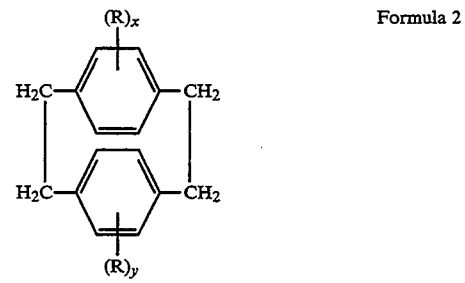

Formula 2 wherein R and X represent the same as the above Formula 1. These materials are the subject of several United States patents such as U.S. Pat. No. 3,117,168 entitled Alkylated Di-p-Xylylenes and U.S. Pat. No. 3,155,712 entitled Cyanated Di-p-Xylylenes and U.S. Pat. No. 3,300,332 entitled Coated Particulate Material and Method for Producing Same all of which are incorporated herein by reference.

The pyrolysis of the vaporous di-p-xylylene occurs upon heating the dimer from about 450° C. to about 700° C. and preferably about 550° C. to about 700° C. Regardless of the pressure employed pyrolysis of the starting di-p-xylylene begins at about 450° C. At temperatures above 700° C. cleavage of the constituent groups can occur resulting in a tri- or polyfunctional species causing cross linking or highly branched polymers. It is preferred that reduced or subatmosphere pressures be employed for pyrolysis to avoid localized hot spots. For most operations pressures within the range of 0.0001 to 10 millimeters Hg are practical. However desired greater pressures can be employed. Likewise inert inorganic vapor diluents such as nitrogen, argon, carbon dioxide and the like can be employed to vary the optimum temperature of operation or to change the total effective pressure of the system.

The diradicals formed in the manner described above are made to impinge upon the surface of the particulate material having surface temperatures below 200° C. and below the condensation temperature of the diradicals present thereby condensing thereon and thus spontaneously polymerizing the diradicals to a uniform coating of a linear polymer having the structure shown in formula 1.

The pharmaceutical for use in the present invention can be any solid, particulate pharmaceutical which requires a timed release application. Suitable pharmaceuticals for use in the present invention include, for instance, ammonium bisphosphate, ammonium chloride, aspirin, colchicine, theophylline, diethylstilbestrol, digestive enzymes such as pancreatin and pepsin, erythromycin, ferrogylcine sulphate, methenamine maleate, oxbile extract, paraminosalicylic acid, phenazopyridiene, proteolitic enzymes such as bromelains, trypsin, and chymotrypsin, potassium chloride, potassium iodide, potassium salicylate, sodium acid pyrophosphate, sodium amino benzoate, sodium biphosphate, sodium chloride U.S.P. or N.F., sodium salicylate, sulfasalzine, sulfoxone sodium, Thyroid USP, ascorbic acid as well as others.

The preferred polymeric coating agent is formed from a commercially available di-p-xylylene composition sold by the Union Carbide Co under the trademark Parylene. The compositions available are Parylene N wherein the above formula both Xs equal 0, Parylene C wherein the one R represents chlorine and the second R represents hydrogen (X=0) and a third composition Parylene D wherein both Rs represent chlorine.

The microencapsulation by vapor deposition can be accomplished in the apparatus shown in FIG. 1 which is similar to an apparatus disclosed in U.S. Pat. No. 3,300,332 previously incorporated by reference.

The apparatus 11 includes an access door which opens to an insulated pyrolysis tube 14. Pyrolysis tube 14 leads to an evacuated chamber 15. Inside the insulated tube 14 is a dish or boat 16 adapted to hold the di-p-xylylene composition. The boat 16 rests on a first heater 17. A second heater 18 encircles a portion of the insulated tube 14 acting as a pyrolysis zone. The tube 14 includes a restricted opening 19 which leads into a rotatable chamber 21 which lies within the evacuated chamber 15. The rotatable chamber 21 is turned by a motor 22 rotating a shaft 23 extending through a vacuum seal 24 into the evacuated chamber 15.

A plurality of baffles or screens 25 are fixed to the walls of the rotating chamber 21 to break up aggregates of core particles. A vacuum pump 26 acts to evacuate the chamber 15 and thus the rotatable chamber 21. A suitable gauge 27 is incorporated to measure the pressure within the evacuated chamber 15.

In operation, the pharmaceutical core particles are placed in chamber 21 and this is rotated while being evacuated. The dimer paraxylylene is placed in boat 16. The heat generated by heater 17 as well as the reduced pressure within the tube 14 causes the di-p-xylylene to evaporate. As it evaporates it is drawn towards the restricted opening 19 and through the portion of the tube 14 which is heated by heater 18. The temperature of the xylylene in boat 16 should be above 170° C. While passing through the portion heated by heater 18, the dimer xylylene is heated to about 700° C. Thus, the dimer is cleaved into its monomeric radicals. The radicals pass through the restricted opening 19 into the interior of the rotated chamber 21. The interior of this chamber is maintained at a lower pressure about 0.14 torn by the vacuum pump 26. The interior of the rotating drum 21 is maintained at room temperature approximately 20° C. The reactive monomer enters the drum 21 through restricted opening 19 and impinges upon the core materials being rotated within the drum. The reduced temperature of the core materials causes the radical to condense on the surface of the core material and polymerize. This creates a very thin coating generally 0.1 to about 10 microns. The baffles or screens 25 act to sift and disperse the pharmaceutical core material to prevent agglomeration.

After the pharmaceutical particles are coated with the Parylene they are removed and processed. They can be compressed with appropriate excipients into tablets or into capsules. With appropriate sterilization they can be processed into an injection form for veterinary uses.

In order to ensure uniformity of coating the coating chamber is advantageously rotated at about 10 to 500 rpms thus continuously tumbling the particles and exposing fresh surface to the condensing di-radicals.

The coating thickness must be controlled for controlling the release properties of the pharmaceutical after application or ingestion. The wall thickness of the polymer coating is a function of both the surface area of the particles being coated as well as the amount of pyrolyzed paraxylylene introduced into the reaction chamber 21.

For purposes of evaluation, the wall thickness of a coating is equal to $\frac{1}{3}$ of the radius of the core particle multiplied by the volume of the wall material divided by the volume of the core material. Thus where the core has an average diameter of 150 microns and the radius of the core is 75 microns one can calculate the thickness of the coating. Presuming for example that the ratio of the volume of the walled material divided by the volume of the core material is 0.15 the thickness would be equal to $\frac{1}{3} \times 75$ microns $\times 0.15 = 3.75$ microns. For purposes of the present invention, the wall thickness should be from about 0.1 micron to about 10 microns and preferably about 0.3 to about 3.0 microns, and the pharmaceutical agent core has a particle size of from about 5 microns to about 2,000 microns and preferably from about 50 microns to about 300 microns and more preferably from about 75 microns to about 150 microns.

Agglomeration of the particles can be controlled by increasing agitation within the reaction chamber, adding large inert particles to bounce around within the reaction chamber or inserting narrow rods within the reaction chamber. If the pharmaceutical powder appears to be initially tacky this can be controlled by adding a small amount of the paraxylylene dimer. An apparently tacky and agglomerated mass of particles actually becomes a free flowing mass of particles upon the application of the paraxylylene dimer.

To evaluate the release properties of pharmaceuticals coated by the parylene polymers the following examples were carried out.

EXAMPLE 1

Potassium chloride (700 g) sieved through a 50 micron screen was used as a starting material. This amount of potassium chloride was placed in the reaction chamber and 28 g of Parylene C dimer placed in the boat 16. The vapor heating temperature was 171° C. The pyrolysis furnace temperature was 690° C. The rotation speed of the reaction chamber was 50 turns per minute. After the chamber pressure reached 20 microns of mercury Parylene C was vaporized and deposited over a 3 hour period. This was repeated five times. After each coating, the potassium chloride plus coating was removed, sieved and replaced with some loss of the material. The amount of material lost was compensated with proportionately less Parylene C dimer placed in the boat. According to the amounts of Parylene evaporated the final amount of parylene plated is shown in Table I. In one run of potassium chloride the Parylene C was replaced with parylene N. In this embodiment 700 g of potassium chloride were placed in the chamber and 14 g of parylene N was placed in the boat. The vapor heating temperature was 171° C. The post heater temperature was 242° C. The paralysis furnace temperature was 690° C. and the rotation speed was 50 rpm.

Figure 2:
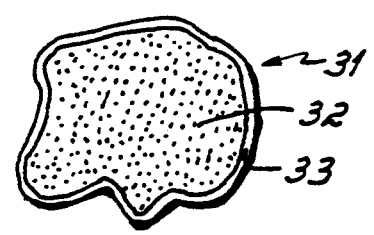
FIG. 2 is a cross-sectional diagrammatic depiction of an active pharmaceutical agent coated with a vapor deposited polymeric film.

As shown in FIG. 2, this produces a micro-encapsulated pharmaceutical 31 having a core 32 (in this case potassium chloride) coated with a Parylene derived polymeric coating 33. The average wall thickness was about 1 micron.

TABLE I

| Grams Core | Grams Wall | % Core/Wall | Parylene |
|---|---|---|---|
| PHARMACEUTICAL 1: POTASSIUM CHLORIDE BATCH ONE | | | |
| 700 | 28 | 4 | C |
| 700 | 14 | 2 | C |
| 461 | 9.3 | 2 | C |
| 388 | 7.75 | 2 | C |
| 700 | 14 | 2 | N |
| POTASSIUM CHLORIDE BATCH TWO | | | |
| 684 | 14 | 2 | C |
| 684 | 14 | 2 | C |
| 474 | 9.5 | 2 | C |
| 408 | 8.2 | 2 | C |
| 343 | 7 | 2 | C |

EXAMPLE 2

Theophylline was coated with parylene C. In this embodiment 500 g of theophylline was placed in the rotatable chamber and 5 g of parylene C was placed in the boat. The vapor heating temperature was 165° C., the pyrolysis furnace was 690° C. and the rotation speed of the chamber was 40 revolutions per minute. After the chamber pressure reached 6 microns $H_2$ the Parylene C was vaporized and deposited over a three hour period. This was repeated five times. The results of this are shown in Table II. The average wall thickness was about 0.2 microns.

TABLE II

| Run | Grams Core | Grams Wall | % Core/Wall | Parylene |
|---|---|---|---|---|
| 1 | 500 | 5 | 1 | C |
| 2 | 500 | 5 | 1 | C |
| 3 | 500 | 5 | 1 | C |
| 4 | 500 | 5 | 1 | C |
| 5 | 500 | 5 | 1 | C |

EXAMPLE 3

Erythromycin was also encapsulated with parylene C. The erythromycin encapsulation provided an unexpected problem in that the pressure as measured by the pressure gauge could not be reduced below about 90 microns. It was presumed that the erythromycin was outgassing. However, after the first coat was placed on the erythromycin the pressure was able to be dropped between 30 and 50 microns. Thus, the 500 g of starting material was coated with parylene C dimer with a vapor heating temperature of 170° C. paralysis temperature of 690° C. and a rotation of the reaction chamber of 40 rpm. The pressure was between 30 and 90 microns for the run. The results again are shown in Table III. The average wall thickness was about 0.5 microns.

TABLE III

| Run | Grams Core | Grams Wall | % Core/Wall | Parylene |
|---|---|---|---|---|
| 1 | 500 | 7 | 1.4 | C |
| 2 | 500 | 7 | 1.4 | C |
| 3 | 500 | 7 | 1.4 | C |
| 4 | 500 | 7 | 1.4 | C |
| 5 | 500 | 7 | 1.4 | C |

To test the dissolution rate of pharmaceuticals coated according to the present invention, theophylline coated with Parylene C according to Example 2 was tested according to the method set out in United States Pharmacopeia 21st Revision 1985 Test 711 utilizing the apparatus No. 2. In this test the medium was 900 milliliters of water, the temperature was maintained at 37° C. and the test apparatus was rotated at 100 rpm. The theophyliine 50 milligrams was weighed accurately and added to the dissolution vessel. Five milliliters of sample was withdrawn at 15, 30, 60, 120, 240, 360 and 1440 minutes and filtered through Wattman No. 1 filter. The samples were then analyzed for theophylline using UV spectrophotometer at 27 nm wave length. The particle size represented below in Table IV is the average particle size in microns of the sample passing through the respective sieves.

TABLE IV

| TIME (MIN) | % RELEASE | | |
|---|---|---|---|
| | MEAN | S.D. | R.S.D. |
| BATCH I: 362.5 um. | | | |
| 15 | 12.94 | 0.321 | 2.48 |
| 30 | 21.69 | 4.950 | 22.80 |
| 60 | 35.94 | 2.610 | 7.27 |
| 120 | 46.78 | 1.410 | 3.02 |
| 240 | 59.38 | 1.224 | 2.06 |
| 360 | 65.53 | 0.694 | 1.06 |
| 1440 | 90.17 | 1.568 | 1.739 |
| BATCH I: 275.0 um. | | | |
| 15 | 11.693 | 0.386 | 3.301 |
| 30 | 16.548 | 0.817 | 4.937 |
| 60 | 23.025 | 1.065 | 4.624 |
| 120 | 27.706 | 2.438 | 8.800 |
| 240 | 38.113 | 2.765 | 7.254 |
| 360 | 48.593 | 4.181 | 8,603 |
| 720 | 61.629 | 5.712 | 8.229 |
| 840 | 65.629 | 4.457 | 6.819 |
| 960 | 70.667 | 4.445 | 6.289 |
| 1440 | 80.593 | 5.838 | 7.244 |
| BATCH I: 215.0 um. | | | |
| 15 | 10.77 | 2.415 | 22.42 |
| 30 | 30.70 | 2.838 | 9.24 |
| 60 | 43.23 | 4.231 | 9.79 |
| 120 | 60.435 | 2.997 | 4.96 |
| 240 | 68.55 | 2.057 | 3.00 |
| 360 | 76.66 | 1.995 | 3.00 |
| 1320 | 92.25 | 2.644 | 2.85 |
| BATCH I: 180.0/ um. | | | |
| 15 | 14.441 | 2.345 | 14.898 |
| 30 | 27.625 | 4.573 | 16.557 |
| 60 | 43.568 | 5.658 | 12.988 |
| 120 | 58.396 | 3,870 | 6.628 |
| 240 | 72.676 | 2.151 | 2.960 |
| 360 | 81.030 | 1.769 | 2.183 |
| 480 | 85.856 | 1.331 | 1.551 |
| 720 | 91.621 | 0.569 | 0.621 |
| 1440 | 97.665 | 1.134 | 1.161 |
| BATCH II: 362.5 um. | | | |
| 15 | 9.648 | 0.658 | 6.827 |
| 30 | 13.990 | 0.462 | 3.304 |
| 60 | 19.020 | 0.720 | 3.785 |

TABLE IV-continued

| TIME (MIN) | % RELEASE | | |
|---|---|---|---|
| | MEAN | S.D. | R.S.D. |
| 120 | 23.435 | 0.734 | 3.133 |
| 240 | 33.965 | 1.273 | 3.748 |
| 360 | 40.118 | 1.872 | 4.667 |
| 720 | 53.745 | 2.806 | 5.221 |
| 1200 | 65.39 | 3.394 | 5.190 |
| 1440 | 69.38 | 3.227 | 4.419 |
| BATCH II: 275.0 um. | | | |
| 15 | 14.740 | 1.333 | 9.049 |
| 30 | 21.451 | 1.807 | 8.426 |
| 60 | 29.490 | 2.076 | 7.041 |
| 120 | 36.258 | 2.112 | 5.827 |
| 240 | 47.889 | 2.589 | 5.407 |
| 360 | 56.693 | 2.699 | 4.761 |
| 480 | 62.954 | 3.323 | 5.278 |
| 720 | 72.086 | 2.838 | 3.936 |
| 1440 | 82.061 | 3.309 | 4.033 |
| BATCH II: 215.0 um. | | | |
| 15 | 11.340 | 2.780 | 24.520 |
| 30 | 27.610 | 1.770 | 6.400 |
| 60 | 39.230 | 3.330 | 8.500 |
| 120 | 50.340 | 3.690 | 7.330 |
| 240 | 61.610 | 4.750 | 7.710 |
| 360 | 72.860 | 5.970 | 7.520 |
| 480 | 79.320 | 5.970 | 7.520 |
| 780 | 91.580 | 5.880 | 6.400 |
| BATCH II: 180.0/ um. | | | |
| 15 | 8.105 | 2.078 | 25.648 |
| 30 | 12.155 | 3.396 | 27.943 |
| 60 | 19.717 | 5.599 | 28.398 |
| 120 | 24.373 | 5.361 | 21.199 |
| 240 | 33.395 | 5.465 | 16.366 |
| 360 | 39.827 | 6.111 | 15.344 |
| 480 | 42.722 | 5.546 | 12.981 |
| 720 | 50.630 | 5.124 | 10.120 |
| 1440 | 60.426 | 5.562 | 9.205 |

Figure 3:
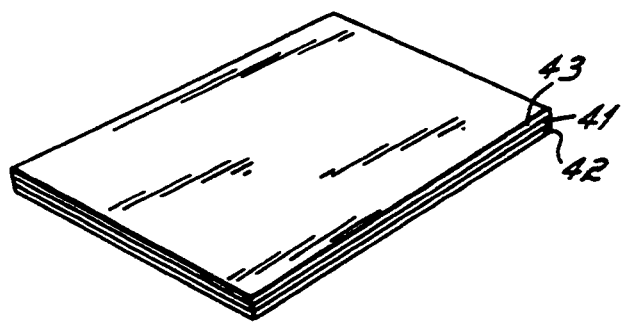
FIG. 3 is a perspective view partially broken away of a dermatological pharmaceutical applicator.

In an alternate embodiment as shown in FIG. 3, the vapor deposited polymer film can be used to coat a layer of a medicament. For example, a thin layer of a dermatological medicament 41 such as antibiotic or steroid can be placed on a first lamina 42 such as a polyethylene sheet or other inert flexible material. A layer 43 of Parylene is then vapor deposited on the dispersed medicament. After deposition the sheet can be placed on the surface of a pathological skin such as burns and the like and various dermatosis. This will provide for sustained release of the antibiotic or medicament.

Figure 4:
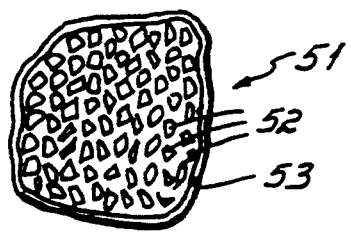
FIG. 4 is a cross-sectional view of a tablet incorporating the coated pharmaceuticals of the present invention.

In another embodiment shown in FIG. 4 the vapor deposited polymer can enhance the effects of medicaments that can be compressed into loosely packed blocks or pellets. In this embodiment pellets 51 of compressed particles 52 (excipients and active pharmaceutical) are coated in the same manner described above by placing the compressed pellets in the reaction chamber and coating with parylene. The Parylene radical monomers by their nature penetrate into tiny cracks and crevices coating the individual particles which form the pellets as well as the pellets themselves as represented by layer 53. This provides a sustained release form of the medicaments.

Figure 5:
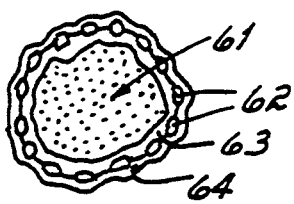
FIG. 5 is a cross-sectional view of an alternate embodiment of the present invention.

Generally the present invention functions with small core particle materials to very large core particle materials. However, when the core particle materials are less than 10 microns say for example 1–10 microns agglomeration is more likely to occur. Accordingly as shown in FIG. 5, with smaller particles an inert core material 61 can be employed. The small pharmaceutical particles 62 are embedded into the surface of the inert core material as it is being coated with a first layer of Parylene. In this embodiment, the core material is simply rotated within the reaction chamber in combination with the pharmaceutical agent. The Parylene radicals are then deposited onto the core materials coating the core materials and permitting the pharmaceutical particles to fix to the surface of the core material. The core material coated with Parylene and having pharmaceutical particles embedded in the Parylene is then coated with a second layer 64 of Parylene further to provide a complete coating of the pharmaceutical agent as well as the core material. This provides a simple method to dilute the pharmaceutical.

Thus, according to the present invention the vapor deposited film coated pharmaceuticals have a large number of potential uses either in forming an orally ingestible pharmaceutical, an injectible pharmaceutical or a dermatological medicament. The surprising ability of the vapor deposited polymeric film to provide a controlled release of the pharmaceutical makes it particularly useful in many different applications. Further, the general inertness of the polymeric film protects the medicament from environmental conditions. This ability to protect the medicament and provide for controlled release of the medicament is a very surprising combination of characteristics.

The vapor deposited films provide for a very controlled application of a very uniform wall thickness about the pharmaceutical agent core. Since the coating is applied molecule by molecule it provides an extremely uniform coating which can be readily controlled.

The preceding description has intended to provide both a description of the invention as well as the preferred mode of practicing the invention known to the inventor at this time. However, the invention should be limited only by the appended claims wherein

I claim:

1. A method of forming a pharmaceutical comprising: coating an inert core material with a vapor deposited polymeric film in combination with minute particles of an active pharmaceutical agent, and subsequently coating said particles of active pharmaceutical agent with a vapor deposited polymeric film, said polymeric film being the solid polymerization product of pyrolyzed vapors of di-p-xylylene, said product having the general repeating units

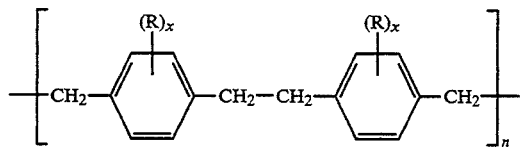

wherein R is an aromatic nuclear substituent, x is a number from 0 to 3 and n is a number from 10–10000 and said polymeric film having a thickness of from about 0.1 microns to about 10 microns.

2. The method as claimed in claim 1, wherein R is selected from the group consisting of alkyl, aryl, alkenyl, amino, cyano, carboxyl, alkoxy, hydroxyl-alkyl, carbalkoxy, hydroxyl, nitro and halogen.

* * * * *